US012082981B2

(12) United States Patent
Sklar

(10) Patent No.: US 12,082,981 B2
(45) Date of Patent: Sep. 10, 2024

(54) SURGICAL ARMREST

(71) Applicant: Frederick H. Sklar, Dallas, TX (US)

(72) Inventor: Frederick H. Sklar, Dallas, TX (US)

(*) Notice: Subject to any disclaimer, the term of this patent is extended or adjusted under 35 U.S.C. 154(b) by 0 days.

(21) Appl. No.: 18/502,841

(22) Filed: Nov. 6, 2023

(65) Prior Publication Data

US 2024/0148468 A1    May 9, 2024

Related U.S. Application Data

(60) Provisional application No. 63/382,696, filed on Nov. 7, 2022.

(51) Int. Cl.
*A47C 7/54* (2006.01)
*A61B 90/60* (2016.01)

(52) U.S. Cl.
CPC ................... *A61B 90/60* (2016.02)

(58) Field of Classification Search
CPC ...................................... A61B 90/60
See application file for complete search history.

(56) References Cited

U.S. PATENT DOCUMENTS

| 2,494,792 | A | 1/1950 | Bloom |
| 2,709,070 | A | 5/1955 | Bielstein |
| 2,966,383 | A | 12/1960 | Boetcker et al. |
| 3,072,118 | A | 1/1963 | Standerwick et al. |
| 3,099,441 | A | 7/1963 | Ries |
| 3,168,274 | A | 2/1965 | Street |
| 3,522,799 | A | 8/1970 | Gauthier |
| 3,604,412 | A | 9/1971 | Gardner |
| 3,699,799 | A | 10/1972 | Hespenhide |
| 3,810,462 | A | 5/1974 | Szpur |
| 3,835,861 | A | 9/1974 | Kees, Jr. et al. |
| 3,923,046 | A | 12/1975 | Heifetz |
| 3,958,558 | A | 5/1976 | Dunphy et al. |
| 4,014,319 | A | 3/1977 | Favre |
| 4,108,426 | A | 8/1978 | Lindstroem et al. |

(Continued)

FOREIGN PATENT DOCUMENTS

| EP | 2316521 | 5/2011 |
| JP | S55-052747 | 4/1980 |

(Continued)

OTHER PUBLICATIONS

International Search Report and Written Opinion dated Mar. 1, 2011 regarding Intl. Patent Application No. PCT/US2011/020906; 9 pgs.

(Continued)

*Primary Examiner* — Amy J. Sterling

(74) *Attorney, Agent, or Firm* — Scott Griggs; Griggs Bergen LLP

(57) ABSTRACT

A surgical armrest is disclosed. In one embodiment, the surgical armrest includes a body having two dorsal mounting brackets attached thereto. Each of the dorsal mounting brackets have an elongated aperture with an armrest member attached thereto. Each of the elongated apertures defines two ranges of rotation substantially parallel to a horizontal axis of the body. Each of the armrest members are configured to support a surgeon's elbow, forearm, wrist, or a combination thereof, during a surgical procedure, such as an operative microsurgery procedure on the skull and brain, for example.

20 Claims, 5 Drawing Sheets

(56) References Cited

U.S. PATENT DOCUMENTS

| | | |
|---|---|---|
| 4,143,652 A | 3/1979 | Meier et al. |
| 4,169,478 A | 10/1979 | Hickmann |
| 4,254,763 A | 3/1981 | Cready et al. |
| 4,281,667 A | 8/1981 | Cosman |
| 4,360,028 A | 11/1982 | Moran et al. |
| 4,444,179 A | 4/1984 | Trippi |
| 4,457,300 A | 7/1984 | Budde |
| 4,465,069 A | 8/1984 | Moran et al. |
| 4,545,572 A | 10/1985 | Day |
| 4,667,660 A | 5/1987 | Eingorn |
| 4,681,559 A | 7/1987 | Hooven |
| 4,700,691 A | 10/1987 | Tari et al. |
| 4,995,401 A | 2/1991 | Bunegin et al. |
| 5,147,287 A | 9/1992 | Jewell et al. |
| 5,197,965 A | 3/1993 | Cherry et al. |
| 5,205,815 A | 4/1993 | Saunders |
| 5,214,815 A | 6/1993 | Agbodoe et al. |
| 5,254,079 A | 10/1993 | Agbodoe et al. |
| 5,269,034 A | 12/1993 | Day et al. |
| 5,276,927 A | 1/1994 | Day |
| 5,284,129 A | 2/1994 | Agbodoe et al. |
| 5,284,130 A | 2/1994 | Ratliff |
| 5,317,771 A | 6/1994 | Cook |
| 5,318,509 A | 6/1994 | Agbodoe |
| 5,326,374 A | 7/1994 | Ilbawi et al. |
| 5,347,894 A | 9/1994 | Fischer |
| 5,529,358 A | 6/1996 | Dinkler et al. |
| 5,537,704 A | 7/1996 | Dinkler |
| 5,564,663 A | 10/1996 | Cook et al. |
| 5,674,186 A | 10/1997 | Guigui et al. |
| D389,242 S | 1/1998 | Boookwaler et al. |
| 5,806,512 A | 9/1998 | Abramov et al. |
| 5,832,926 A | 11/1998 | Towlen |
| 5,984,864 A | 11/1999 | Fox et al. |
| 6,117,143 A | 9/2000 | Hynes et al. |
| 6,179,846 B1 | 1/2001 | McFadden |
| 6,283,934 B1 | 9/2001 | Borgesen |
| 6,306,085 B1 | 10/2001 | Farascioni |
| 6,306,146 B1 | 10/2001 | Dinkler |
| 6,315,783 B1 | 11/2001 | Katz et al. |
| 6,368,330 B1 | 4/2002 | Hynes et al. |
| 6,381,783 B2 | 5/2002 | Reinhardt et al. |
| 6,416,468 B2 | 7/2002 | Deckman et al. |
| 6,463,765 B2 | 10/2002 | Blakely |
| 6,557,195 B2 | 5/2003 | Dinkler |
| 6,584,630 B1 | 7/2003 | Dinkler |
| 6,594,839 B1 | 7/2003 | Papay |
| 6,602,190 B2 | 8/2003 | Dobrovolny |
| 6,619,747 B2* | 9/2003 | Ko .................. A47C 9/025 297/411.31 |
| 6,629,982 B2 | 10/2003 | Day et al. |
| 6,684,428 B2 | 2/2004 | Grotehuis et al. |
| 6,698,044 B2 | 3/2004 | Greenfield et al. |
| 6,770,082 B2 | 8/2004 | Dominguez et al. |
| 6,786,461 B1* | 9/2004 | Tsai .................. B43M 99/00 248/292.12 |
| 7,024,892 B2 | 4/2006 | Blakely |
| 7,117,551 B1 | 10/2006 | Dinkler, II et al. |
| 7,222,826 B1* | 5/2007 | Berglund .......... A47B 21/0314 248/118 |
| 7,229,451 B2 | 6/2007 | Day et al. |
| 7,232,411 B2 | 6/2007 | Dinkler, II et al. |
| 7,326,177 B2 | 2/2008 | Williamson, IV et al. |
| 7,452,032 B1* | 11/2008 | Roleder .................. A61G 15/12 297/182 |
| 7,507,244 B2 | 3/2009 | Dinkler |
| 7,510,533 B2 | 3/2009 | Mauge et al. |
| 7,552,492 B2 | 6/2009 | Rolfes et al. |
| 7,730,563 B1 | 6/2010 | Sklar et al. |
| 7,823,843 B2* | 11/2010 | Oberlaender ...... F16M 11/2092 248/278.1 |
| 7,866,613 B2* | 1/2011 | Cramer .................. A61G 5/125 248/292.12 |
| 7,882,574 B2 | 2/2011 | Arsenault |
| 7,945,970 B2 | 5/2011 | Belluye et al. |
| 7,949,394 B2 | 5/2011 | Salo et al. |
| 8,037,884 B2 | 10/2011 | Weinstein et al. |
| 8,105,256 B1 | 1/2012 | Ariza |
| 8,257,289 B2 | 9/2012 | Vess |
| 8,292,856 B2 | 10/2012 | Bertrand et al. |
| 8,322,342 B2* | 12/2012 | Soto .................. A61G 13/0072 128/845 |
| 8,356,601 B2* | 1/2013 | Hunter, Jr. .......... A61G 13/1235 128/845 |
| 8,568,195 B1 | 10/2013 | Schindler |
| 8,646,452 B2 | 2/2014 | Sklar |
| 8,801,711 B2 | 8/2014 | Solomon et al. |
| 9,033,909 B2 | 5/2015 | Aihara |
| 9,211,224 B2 | 12/2015 | Sklar |
| 9,216,125 B2 | 12/2015 | Sklar |
| 9,717,637 B2* | 8/2017 | Bucher .................. A61G 5/122 |
| 9,717,890 B2 | 8/2017 | Holper et al. |
| 9,925,360 B2 | 3/2018 | Ludin et al. |
| 10,743,954 B2 | 8/2020 | Sklar |
| 10,792,183 B2* | 10/2020 | Hoffman .................. A61F 5/3769 |
| 10,940,071 B1* | 3/2021 | Hunter, Jr. .......... A61G 13/101 |
| 11,103,683 B1 | 8/2021 | Sklar |
| 11,154,695 B2 | 10/2021 | Sklar |
| 11,234,885 B2* | 2/2022 | Lane, II .............. A61G 13/1295 |
| 11,324,933 B2 | 5/2022 | Sklar |
| 11,389,630 B2 | 7/2022 | Sklar |
| 11,471,231 B2 | 10/2022 | Sklar et al. |
| 11,678,947 B2 | 6/2023 | Sklar |
| 2001/0029379 A1 | 10/2001 | Grotehuis et al. |
| 2002/0042619 A1 | 4/2002 | Dominguez et al. |
| 2002/0128577 A1* | 9/2002 | Smart .................. A61G 13/12 602/32 |
| 2002/0151907 A1 | 10/2002 | Day et al. |
| 2004/0097985 A1 | 5/2004 | Day et al. |
| 2005/0075650 A1 | 4/2005 | Dinkler |
| 2005/0277832 A1 | 12/2005 | Foley et al. |
| 2006/0076464 A1 | 4/2006 | Van |
| 2006/0255220 A1 | 11/2006 | Skripps |
| 2008/0139959 A1 | 6/2008 | Miethke et al. |
| 2008/0172791 A1* | 7/2008 | Walczyk .................. A61G 13/12 5/624 |
| 2008/0269777 A1 | 10/2008 | Appenrodt et al. |
| 2009/0138064 A1 | 5/2009 | Horn |
| 2009/0192432 A1 | 7/2009 | Frazer |
| 2009/0204019 A1 | 8/2009 | Ginggen et al. |
| 2009/0254017 A1 | 10/2009 | Dumpson et al. |
| 2009/0287084 A1 | 11/2009 | Ragauskas et al. |
| 2009/0299258 A1 | 12/2009 | Cureington-Sims |
| 2010/0117281 A1 | 5/2010 | Doyle |
| 2011/0054373 A1 | 3/2011 | Reiley |
| 2011/0066072 A1 | 3/2011 | Kawoos et al. |
| 2011/0168184 A1 | 7/2011 | Sklar |
| 2012/0226215 A1 | 9/2012 | Hsu et al. |
| 2013/0085400 A1 | 4/2013 | Oliveira et al. |
| 2013/0095730 A1 | 4/2013 | Jensen |
| 2014/0378774 A1 | 12/2014 | Wooster |
| 2015/0005800 A1 | 1/2015 | Anite |
| 2015/0268673 A1 | 9/2015 | Farzbod et al. |
| 2019/0009014 A1 | 1/2019 | Chen et al. |
| 2020/0061355 A1 | 2/2020 | Barnea et al. |
| 2022/0257913 A1 | 8/2022 | Sklar |

FOREIGN PATENT DOCUMENTS

| | | |
|---|---|---|
| JP | H09-075369 | 3/1997 |
| JP | H09-147142 | 6/1997 |
| WO | 2018227022 | 12/2018 |
| WO | 2019241753 | 12/2019 |

OTHER PUBLICATIONS

International Search Report and Written Opinion dated Oct. 18, 2012 regarding Intl. Patent Application No. PCT/US12/47894; 11 pgs.

International Search Report and Written Opinion dated May 6, 2013 regarding Intl. Patent Application No. PCT/US13/26207; 16 pgs.

(56) References Cited

OTHER PUBLICATIONS

International Search Report and Written Opinion dated Jun. 30, 2021 regarding Intl. Patent Application No. PCT/US21/17365; 12 pgs.
Turnbull et al.; "Post-dural puncture headache: pathogenesis, prevention and treatment"; British Journal of Anaesthesia; 2003; 91(5); pp. 718-729.
International Search Report and Written Opinion dated Aug. 31, 2018 regarding Intl. Patent Application No. PCT/US18/36558; 12 pgs.
Farlex Partner Medical Dictionary. S.v. "costal marin." Retrieved Jan. 11, 2016 from http://medical-dictionary.thefreedictionary.com/costal+margin; 1 pg.
Sklar et al.; "The Use of Abdominal Binders to Treat Over-Shunting Headaches"; J. Neurosurg. Pediatr.; Jun. 2012; 9(6); pp. 615-620; dol: 10.3171/2012.2.PEDS11146; Children's Medical Center, Dallas, Texas, USA.
International Search Report and Written Opinion dated Feb. 8, 2024 for International Application No. PCT/US2023/078947; 7 pp.

\* cited by examiner

SURGICAL ARMREST

PRIORITY STATEMENT & CROSS-REFERENCE TO RELATED APPLICATIONS

This application claims priority from U.S. Patent Application No. 63/382,696, entitled "Surgical Armrest" and filed on Nov. 7, 2022, in the name of Frederick H. Sklar; which is hereby incorporated by reference for all purposes.

This application discloses subject matter related to the subject matter disclosed in the following commonly owned, co-pending patent applications: U.S. application Ser. No. 18/502,795, entitled Patent "Surgical Universal Headrest Including Skull Pin Holder Assembly" and filed on Nov. 6, 2023, in the name of Frederick H. Sklar; U.S. patent application Ser. No. 18/502,807, entitled "Surgical Universal Headrest Including Skull Pin Holder Assembly" and filed on Nov. 6, 2023, in the name of Frederick H. Sklar; U.S. patent application Ser. No. 18/502,811, entitled "Surgical Universal Headrest Including Skull Pin Holder Assembly" and filed on Nov. 6, 2023, in the name of Frederick H. Sklar; U.S. patent application Ser. No. 18/502,815, entitled "Surgical Universal Headrest Including Skull Pin Holder Assembly" and filed on Nov. 6, 2023, in the name of Frederick H. Sklar; U.S. patent application Ser. No. 18/502,820, entitled "Base Station Assembly for an Operating Room Table" and filed on Nov. 6, 2023, in the name of Frederick H. Sklar; U.S. patent application Ser. No. 18/502,825, entitled "Base Station Assembly for an Operating Room Table" and filed on Nov. 6, 2023, in the name of Frederick H. Sklar; U.S. patent application Ser. No. 18/502,839, entitled "Base Station Assembly for an Operating Room Table" and filed on Nov. 6, 2023, in the name of Frederick H. Sklar; all of which are hereby incorporated by reference, in entirety, for all purposes.

TECHNICAL FIELD OF THE INVENTION

This invention relates, in general, to surgical appliances and, in particular, to a surgical armrest used to support a surgeon's forearms, wrists, or a combination thereof, during a surgical procedure, such as an operative microsurgical procedure on a skull and brain.

BACKGROUND OF THE INVENTION

Evidence suggests that surgeon arm, forearm, wrist, neck, shoulders and general body posture while operating contributes to strain and discomfort during the operative procedure, and these unpleasant distractions may interfere with the surgeon's ability to perform the operative procedure at his or her best. Surgeons performing microsurgery may be particularly susceptible to these problems due to extended periods of static posture and the requirement of enhanced surgical accuracy while working under high magnification with the operating microscope. Accordingly, there is a need for improved surgical armrests that may help avoid these unpleasant and distracting problems during long and/or tedious operations, especially while performing microsurgery.

SUMMARY OF THE INVENTION

It would be advantageous to achieve a surgical armrest used to support a surgeon's forearms, wrists, or a combination thereof, during a surgical procedure, such as an operative microsurgical procedure on a skull and brain. It would also be desirable to enable mechanical and medical-based solutions that would provide adjustability of such an armrest and mitigate spatial restrictions by providing enhanced surgeon control without the required assistance of others who are not scrubbed and without increased risk of contamination of the surgical field.

In one aspect, some embodiments are directed to a surgical armrest that includes a body having two dorsal mounting brackets attached thereto. Each of the dorsal mounting brackets have an elongated aperture with an armrest member attached thereto. Each of the elongated apertures defines two ranges of rotation substantially parallel to a horizontal axis of the body. Each of the armrest members are configured to support a surgeon's elbow, forearm, wrist, or a combination thereof, during a surgical procedure, such as an operative microsurgical procedure on the skull and brain, for example.

In another aspect, some embodiments are directed to a surgical armrest that includes a body having two dorsal mounting brackets attached thereto. One of the dorsal mounting brackets has an elongated aperture with an armrest member attached thereto. Therefore, only one of the armrests is adjustable, with the adjustable armrest having two ranges of rotation substantially parallel to a horizontal axis of the body. Each of the armrest members are configured to support a surgeon's elbow, forearm, wrist, or a combination thereof, during a surgical procedure, such as an operative microsurgical procedure on the skull and brain, for example.

In another aspect, some embodiments are directed to a surgical armrest that includes a body having two armrests attached thereto. The two armrests are static. Similar to the other embodiments, each of the armrest members are configured to support a surgeon's elbow, forearm, wrist, or a combination thereof, during a surgical procedure, such as an operative microsurgical procedure on the skull and brain, for example. Therefore, by way of various embodiments, the surgical armrest presented herein may have various combinations of static and dynamic armrests. These and other aspects of the invention will be apparent from and elucidated with reference to the embodiments described hereinafter.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which.

DETAILED DESCRIPTION OF THE INVENTION

Figure 1:
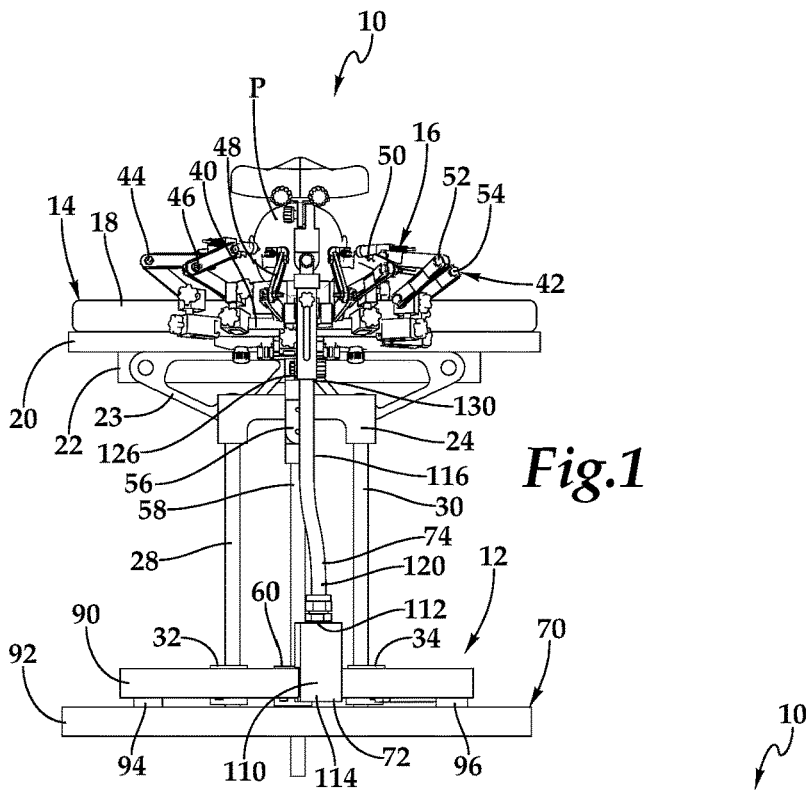
FIG. 1 is a cephalic elevation view of one embodiment of the cranial end of an operating room table with a surgical head holder and a base station assembly to facilitate the use of various surgical accessories, a surgical armrest, during a surgical procedure, such as an operative procedure on a skull and brain of a patient, according to the teachings presented herein.

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention, and do not delimit the scope of the present invention.

Referring initially to FIG. 1 through FIG. 6, therein is depicted one embodiment of a surgical armrest 10 attached to a base station assembly 12 being utilized with an operating room table 14 and a surgical head holder 16. The base station assembly 12, the operating room table 14, and the surgical head holder 16 may be utilized for skull stabilization during a surgical operation, such as neurosurgical, otolaryngological, and orthopedic procedures, for example. As will be discussed in further detail hereinbelow, the surgical armrest 10 is configured to support a surgeon's forearms, wrists, or a combination thereof, during a surgical procedure, and, in particular, during a microsurgical procedure, such as an operative microsurgery procedure on a skull and brain, for example. It should be appreciated, however, that the surgical armrest 10 presented herein may be utilized with a variety of base station assemblies, including the base station assembly 12, and by way of further example, the teachings of FIG. 17 hereinbelow.

The operating room table 14 provides the surgical equipment necessary on which a patient P lies during the surgical operation. As shown, the operating room table 14 includes an operating room table pad 18 supraposed to an operating room tabletop 20 including a support block 22 connected to a cross bar 24 by one or more horizontal support members, with a horizontal support member 26 being depicted to show the support. It should be appreciated, however, that although not shown, the horizontal support member 26 may include a plurality of horizontal support sub-members. Vertical support members 28, 30 extend ventrally from the cross bar 24 with the vertical support member 28 having a support block 32 and the vertical support member 30 having a support block 34. The support blocks 22, 32 and cross bars 24, 34 may each be selectively adjustable with knobs (not shown) to assist surgical staff with proper alignment and placement of the components of the base station 12, the surgical headrest 40, and various surgical accessories on the operating room table 14. By way of example, the support blocks 32, 34 provide for alignment and placement in the dorsal-ventral direction as well as the caudal-cephalic direction. It should be appreciated that although one embodiment of the operating room table 14 is illustrated and described, the teachings presented herein are applicable to other operating room table configurations and designs. By way of example, and not by way of limitation, one alternative design is presented in FIG. 17.

The surgical head holder 16 includes a headrest 40, which may be a universal headrest, that generally functions in a plane approximately parallel to a top of the operating room table 14; although, the headrest 40 may be tilted as necessary for positioning of the patient and for reasons related to the surgical approach to be used. The headrest 40 may carry the weight of a head of the patient P, resting on a special gel pad(s) superposed on the dorsal surface of the headrest 40. The surgical head holder 16 includes a skull pin holder assembly 42 having skull pin holders 44, 46, 48, 50, 52, 54, or more, depending on the thinness of the patient's skull. The skull pin holder assembly 42 contributes to preventing any movement of the head of the patient P, thereby allowing safe microsurgery, and enabling accurate employment of image guidance technology. As shown, the headrest 40 is supported by a support block 56 having a vertical support member 58 extending therefrom that connects to the base station assembly 12 with the use of a support block 60. The support blocks 56, 60 may each be selectively adjustable with knobs (not shown) to assist surgical staff with proper alignment and placement of the components of the surgical head holder 16. It should be appreciated that although one embodiment of the surgical head holder 16 is illustrated and described, the teachings presented herein are applicable to other operating room table configurations and designs.

Continuing to refer to FIG. 1 through FIG. 6, in some embodiments, the base station assembly 12 includes a base station 70 having a selectively moveable clamp 72 attached thereto. The selectively moveable clamp 72 has a vertical support arm 74 extending therefrom. The vertical support arm 74 may include a short, tight "S" curve S to assist in positioning of the vertical support arm 74 and the surgical armrest 10. It should be appreciated that FIGS. 1-5 depict an exaggerated curve S that may be tighter in some embodiments. Whether the curve S is tighter or more open in some embodiments is an option for the surgeon. In one implementation, the base station 70 includes interconnected horizontal support members 80, 82, 84, 86. The interconnected horizontal support members 80, 86 of the base station 70 join the base station assembly 12 to the operating room table 14.

Figure 17:
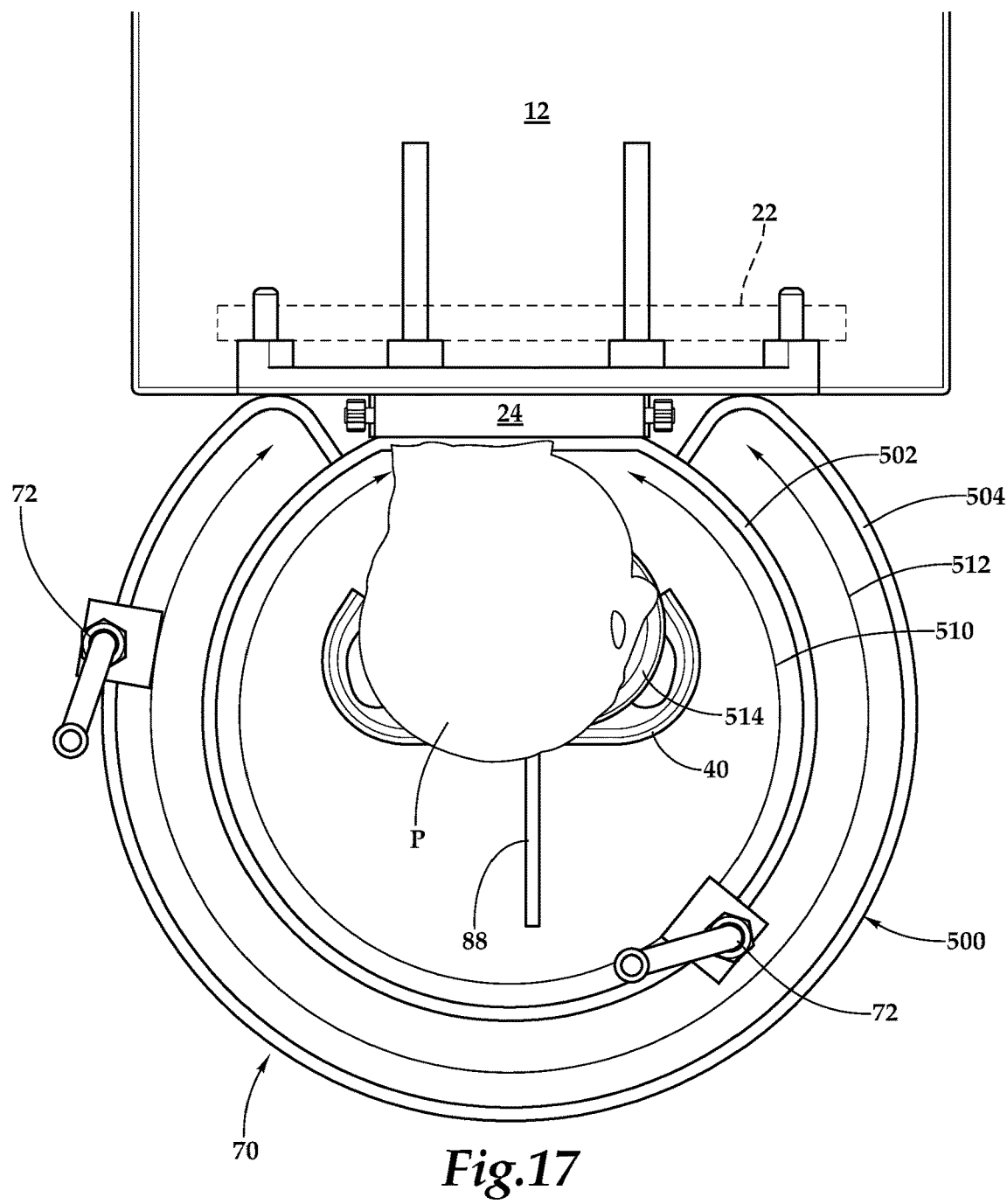
FIG. 17 is a top plan view of a further base station embodiment which provides a maximal travel arc of 286° for a selectively moveable clamp supporting the surgical armrest, for instance, on the upper arcuate rail, or alternatively, 274° on the lower arcuate rail.

An arcuate rail member 90, which may be an upright bar, is coupled to the interconnected horizontal support member 80. As shown, a passage 91 is located between the horizontal support member 84 and the arcuate rail member 90 to provide for the movement of the selectively moveable clamp 72 around the orbit of the arcuate rail member 90. A second arcuate rail member 92, which may also be an upright bar, is coupled to the interconnected horizontal support member 80 at ventral tabs 94, 96. The use of the ventral tab 94 and the ventral tab 96 permit the arcuate rail member 90 and the arcuate rail member 92 to be vertically offset. In some embodiments, the selectively moveable clamp 72 includes a body 110 having an upper end 112 and a lower end 114. The body 110 accommodates a width of a rail in the form of an arcuate rail member 90 of the base station 70. Rollers (not shown) are secured to the body 110 and configured to be placed on the arcuate rail member 90, for example. It should be appreciated that depending on the embodiment selected by the surgeon, the base station 70 may have one arcuate rail member, i.e., arcuate rail member 90 or arcuate rail member 92, or the base station 70 may have two arcuate rail members, i.e., arcuate rail members 90, 92. In a further embodiment of base station 70, which is best shown in FIG. 17, the base station 70 also has two arcuate rails 90, 92, each having the radius $r_1$ and radius $r_2$, respectively, as previously considered; however, as shown in FIG. 17, the respective arcuate pathways for selectively moveable clamps 72 on arcuate rails 90, 92 are significantly longer than those of the other embodiments. It is therefore suggested that microneurosurgeons may consider the setup arrangement with this base station a distinct advantage, especially with the addition of a surgical armrest 10.

Continuing again to refer to FIG. 1 through FIG. 6, the vertical support arm 74 includes an elongated member 116 having ends 118, 120 with a channel 122 therethrough. A ball bearing train 124 is located in the channel 122 from proximate the end 118 to proximate the end 120. The ball bearing train 124 has an upper end 125 proximate the end 118 and a lower end 127 proximate the end 120. The elongated member 116 is configured to selectively actuate between a release position and an engagement position by actuation of a control knob 126. In the release position, the selectively moveable clamp 72 is actuated to an open position where the selectively moveable clamp 72 may slide on the arcuate rail member 90 and be repositioned. On the other hand, in the engagement position, the selectively moveable clamp 72 is in a closed position and locked in position on the arcuate rail member 90. The control knob 126 is located within a vertical slot 130 of a cylindrical sheath 132 that contains the top end of the elongated member 116. A cabined recess 134, which is depicted as presenting a bulge, may be positioned opposite to the slot 130 to accept and house the distal end of the control knob 126. A control knob 128 may provide adjustment by permitting a height of the vertical support arm 74 to be raised or lowered by adjusting a position of the cylindrical sheath 132 that contains the top end of the elongated member 116.

As will be discussed in further detail hereinbelow, at the end 118 of the vertical support arm 74 provides a coupling to the surgical armrest 10.

In some operational implementations, the base station assembly 12 supports various surgical accessories during a surgical procedure, such as an operation on the skull and brain. Depending on the embodiment, the base station 70 provides one or two horizontal orbits centered on the headrest 40 for the selectively moveable clamp 72 to be adjustably positioned by actuation of the control knob 126 within the vertical slot of the cylindrical sheath 132 on the vertical support arm 74. Additionally, the height of the vertical support arm 74 may be adjusted as required via the control knob 128. Furthermore, the vertical support arm 74 can be selectively rotated and/or slightly tilted at its connection to the dorsal surface 112 of the moveable clamp 72. Because of the curved geometry of the vertical support arm 74, both such maneuvers may respectively move the supported surgical accessory closer or farther away from the operative site. This versatility in positioning mitigates spatial restrictions while providing enhanced surgeon control without the required assistance of others who are not scrubbed and without increased risk of contamination of the surgical field.

Referring now to FIG. 7A through FIG. 12, in some embodiments, the surgical armrest 10 includes a body 150 having a dorsal surface 152, a ventral surface 154, a lateral end 156, a lateral end 158, a caudal end 160, and a cephalic end 162. As shown, the body 150 also has a horizontal axis $A_1$ therethrough and a vertical axis $A_2$ therethrough. The horizontal axis $A_1$ is perpendicular to the vertical axis $A_2$. The body 150 also has a medial line M, which is in alignment with the horizontal axis $A_1$ and positioned between the lateral end 156 and the lateral end 158, as best seen in FIG. 7B. A ventral mounting bracket 164 is secured to the ventral surface 154 of the body 150. The ventral mounting bracket 164 includes an elongated slot 166 defining a range of caudal-to-cephalic sliding motion, as shown by arrow C-C, of the body 150 with respect to a support member 168 which is secured thereto by a ventral glide 170. The elongated slot 166 also defines a range of dorsal-to-ventral tilt, as shown by angle D-V, of the body 150 with respect to the support member 168. In one implementation, the ventral mounting bracket 164 is perpendicular to the horizontal axis $A_1$. The elongated slot 166 may be a shape such as a linear slot or arcuate slot, for example. The support member 168 couples to the vertical support arm 74. In one implementation, the attachment member 252 and the support member 168 may be at least partially or fully integrated. Further, various adjustable couplings may be utilized to secure the support member 168 to the attachment member 252 of the vertical support arm 74.

Accordingly, the elongated slot 166 of the ventral mounting bracket 164 provides radial adjustment of the body 150 of the surgical armrest 10 positioned on one of the arcuate rail members 90 or 92, locked in place with the selectively moveable clamp 72. This allows the surgeon to position his or her hands appropriately proximate to the focus of the operation. Furthermore, the surgeon may prefer to position the selectively moveable clamp 72 of the vertical support arm 74 of the surgical armrest 10 on the outside arcuate rail member 92 of the base station 12 and the various selectively moveable clamps 72 with their respective vertical support arms 74 for brain retractors, for example, on the inner arcuate rail member 90. In this way, the surgeon can elect to change the angle of the surgical attack at any time by accordingly repositioning the surgical armrest 10 anywhere on the 220° arc of the outer arcuate rail member 92 of this particular embodiment without having to interfere or move any of the vertical support arms 74 holding brain retractors, which are nesting on the inner arcuate rail member 90.

Moreover, when operating on tiny babies such as small infants, term infants, or premature infants, the surgeon may require additional radial adjustment capability to position the surgical armrest 10 close enough to the surgical site so that the surgeon can operate with standard microsurgical instrumentation while resting his forearms and/or wrists on the surgical armrest 10. Therefore, in another embodiment that allows for this radial positioning adjustment of the armrest 10 toward a tiny infant, for example, the slot 166 is extended caudally, as demonstrated in FIG. 15. Moreover, surgeons may prefer to use the surgical armrest 10 with the extended slot 166 on all patients, because it provides greater radial adjustability.

A dorsal mounting bracket 180 having an elongated aperture 181 is secured to the dorsal surface 152 of the body 150. The elongated aperture 181 may be a shape such as a linear slot or an arcuate slot, for example. An armrest member 184 is secured to the dorsal mounting bracket 180 at the elongated aperture 181 by dorsal glides 186, 187 having a linking lock bar 182 interposed therebetween. The linking lock bar 182 is shaped to fit the elongated aperture 181 and shaped to rest against each of the dorsal glides 186, 187. The armrest member 184 is configured to support a body part, such as an elbow, forearm, wrist, or combinations thereof. The dorsal glide 186 connects the dorsal mounting bracket 180 to the body 150 and the dorsal glide 187 connects the dorsal mounting bracket 180 to the armrest 184. This arrangement provides two points of rotation. That is, a point of rotation at the dorsal glide 186 and a point of rotation at the dorsal glide 187. Both points of rotation at the dorsal glide 186 and the dorsal glide 187 are substantially parallel to the horizontal axis $A_1$ for the armrest member 184 with respect to the body 150. The two points of rotation are represented as a rotation $R_{RB}$ and a rotation $R_{RA}$.

A dorsal mounting bracket 190 is secured to the dorsal surface 152 of the body 150 and the dorsal mounting bracket 190 includes an elongated aperture 191 having a linking lock bar 192 therein. The elongated aperture 191 may be a shape such as a linear slot or an arcuate slot, for example. An armrest member 194 is secured to the dorsal mounting bracket 190 at the elongated aperture 191 by dorsal glides 196, 197. Similar to the armrest 184, the armrest member 194 is configured to support a body part, such as an elbow, forearm, wrist, or combinations thereof. The dorsal glide 196 connects the dorsal mounting bracket 190 to the body 150 and the dorsal glide 197 connects the dorsal mounting bracket 190 to the armrest 184. This arrangement provides two points of rotation. That is, a point of rotation at the dorsal glide 196 and a point of rotation at the dorsal glide 197. Both points of rotation at the dorsal glide 196 and the dorsal glide 197 are substantially parallel to the horizontal axis $A_1$ for the armrest member 194 with respect to the body 150. The two points of rotation are represented as a rotation $R_{LB}$ and a rotation $R_{LA}$.

In the illustrated embodiment, the armrest member 184 includes a base member 198 opposite a ridge member 200. The armrest member 184 also includes a medial member 202 extending ventrally and medially from the ridge member 200 to the base member 198. A lateral concave member 204 extends ventrally and laterally from the ridge member 200 and a lateral convex member 206 extends from the lateral concave member 204 to the base member 198. A caudal transition member 208 extends from the ridge member 200 to the base member 198. On the opposite side, a cephalic transition member 210 extends from the ridge member 200 to the base member 198. With this arrangement, the armrest member 184 has an elevated portion 212 and a concave portion 214. In particular, the elevated portions 212, 232 are in the same plane as the medial members 202, 222. With respect to the armrest member 184, with this arrangement, the armrest member 184 has a medial member 202 that is medial, flat and elevated and adjacent to the concave portion 214.

Similar to the armrest member 184, the armrest member 194 has a base member 218 opposite a ridge member 220 with the armrest member 194 including a medial member 222 extending ventrally and medially from the ridge member 220 to the base member 218. The armrest member 194 includes a lateral concave member 224 extending ventrally and laterally from the ridge member 220. A lateral convex member 226 extends from the lateral concave member 224 to the base member 218. A caudal transition member 228 extends from the ridge member 220 to the base member 218. On the opposite side, a cephalic transition member 230 extends from the ridge member 220 to the base member 218. With this arrangement, the armrest member 194 has an elevated portion 232 and a concave portion 234.

As illustrated, the dorsal mounting bracket 180 may be secured to the dorsal surface 152 of the body 150 proximate the caudal end 160 between the medial line M and the lateral end 156. Similarly, the dorsal mounting bracket 190 may be secured to the dorsal surface 152 of the body 150 proximate the caudal end 160 between the medial line M and the lateral end 158.

Figure 7A:
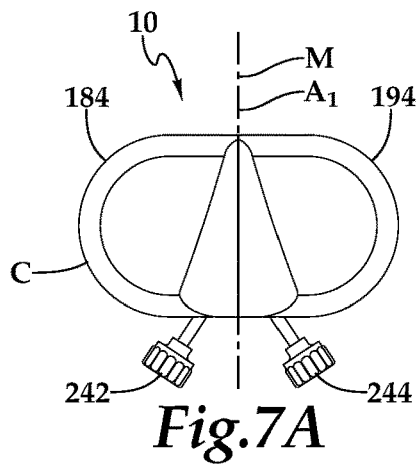
FIG. 7A is a dorsal plan view of the surgical armrest depicted in FIG. 1 in a closed position.
Figure 7B:
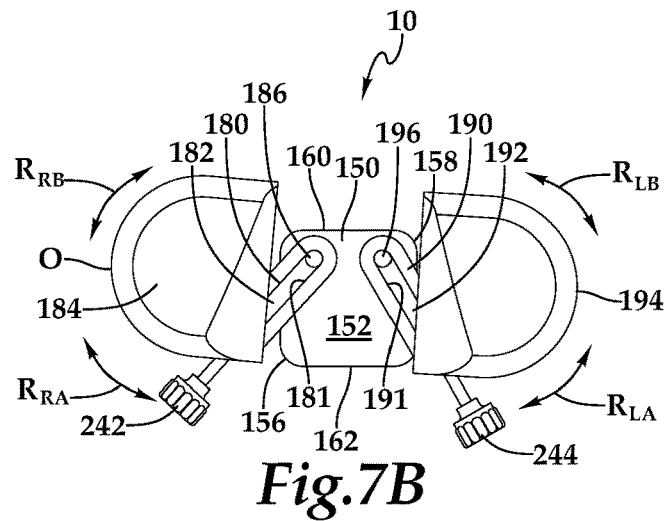
FIG. 7B is a dorsal plan view of the surgical armrest depicted in FIG. 1 in an open position.
Figure 8A:
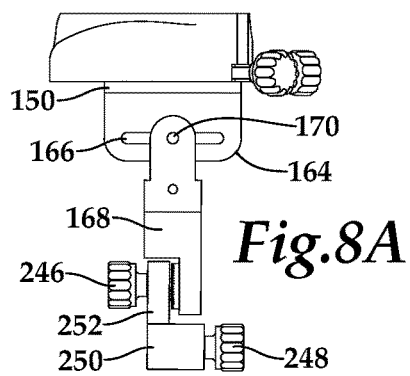
FIG. 8A is a lateral elevation view of the surgical armrest depicted in FIG. 1 in a closed position at a first angle of tilt.
Figure 8B:
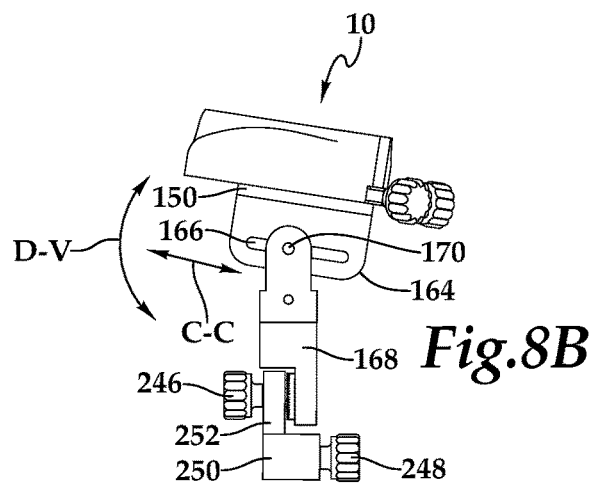
FIG. 8B is a lateral elevation view of the surgical armrest depicted in FIG. 1 in an open position at a second angle of tilt.
Figure 9:
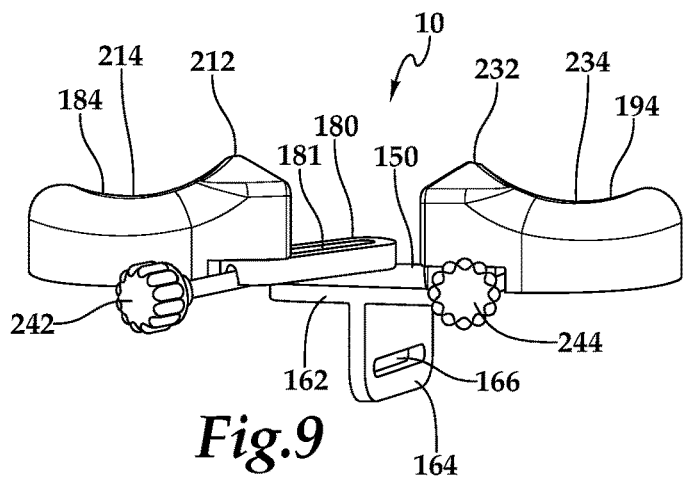
FIG. 9 is a cephalic perspective view of the surgical armrest depicted in FIG. 1 in an open position.
Figure 10:
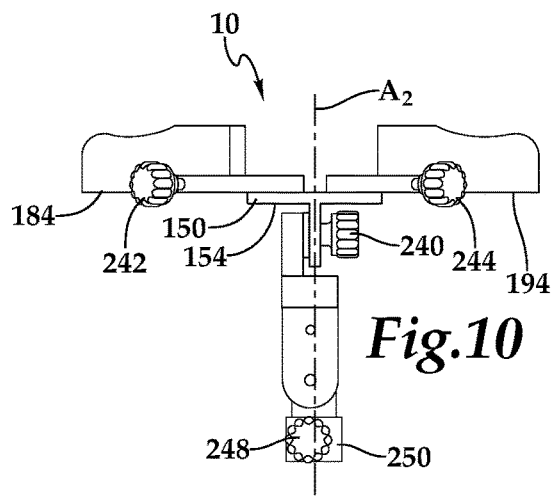
FIG. 10 is a cephalic elevation view of the surgical armrest depicted in FIG. 1 in an open position.
Figure 11:
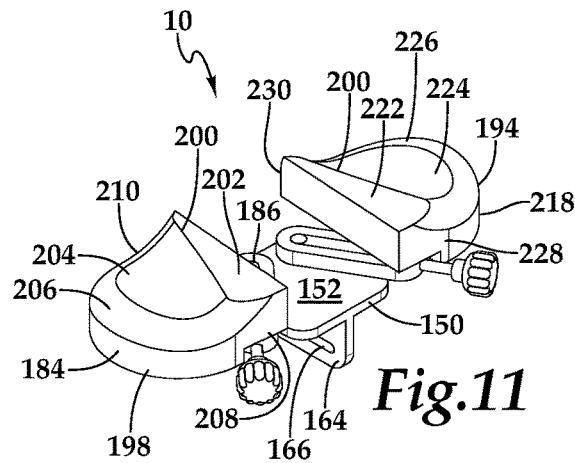
FIG. 11 is dorsal cephalic perspective view of a portion of the surgical armrest depicted in FIG. 1.
Figure 12:
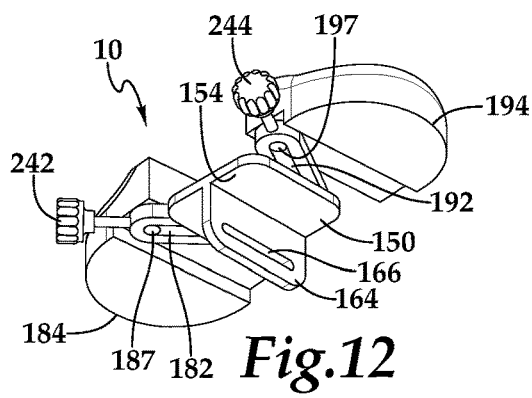
FIG. 12 is a ventral cephalic perspective view of a portion of the surgical armrest depicted in FIG. 1.

In some embodiments, the armrest member 184 and the armrest member 194 include a closed position C, as best seen in FIG. 7A, where the medial member 202 and the medial member 222 are adjacent. Furthermore, the medial member 202 and the medial member 222 may have complimentary forms such that, in the closed position C, the adjacent medial members 202, 222, which may be flat, cooperate to provide support for a body part, such as an elbow, forearm, wrist, or combinations thereof. In other embodiments, the armrest member 184 and the armrest member 194 include an open position O, as best seen in 7B and FIG. 9 through FIG. 12, where the medial member 202 and the medial member 222 are separated due to the active rotation and positioning facilitated by one or more of the rotations $R_{LB}$, $R_{LA}$, $R_{RB}$, and $R_{RA}$. It should be appreciated that configuration of the armrests 184, 194 of the surgical armrest 10 depicted in FIG. 9 is unlikely to be utilized during an operation. Rather, the configuration of the armrests 184, 194 in FIG. 9 is shown for exemplary reasons as an example of the range of movement of the armrests 184, 194.

Referring now to FIG. 6 through FIG. 12, as shown, in operation, adjustments to the surgical armrest 10 are made by a series of hand adjustable knobs 240, 242, 244, 246, 248. More particularly, the hand adjustable knob 240 is coupled to the surgical armrest 10 at the ventral mounting bracket 164 to control a position of the body 150 with respect to the support member 168. The adjustments of the hand adjustable knob 240 define the range of caudal-to-cephalic sliding motion, as shown by arrow C-C, of the body 150 with respect to the support member 168 which is secured thereto by the ventral glide 170. The adjustment of the hand adjustable knobs 240 also define the range of dorsal-to-ventral tilt, as shown by angle D-V, of the body 150 with respect to the support member 168. The adjustments of the hand adjustable knobs 246, 248 change the tilt in a coronal plane and rotation around the axis of the cylindrical sheath 132, respectively. More particularly, a ring member 252 is set over the cylindrical sheath 132 in a circumscribing manner to provide for rotation around the vertical support arm 74. An extension member 252 extends vertically from the ring member 252. The hand adjustable knob 248 tightens or loosens the ring member 252 to allow for rotation around the vertical support arm 74.

The hand adjustable knob 242 is coupled to the dorsal mounting bracket 180 to permit control and positioning of the armrest member 184 with respect to the dorsal mounting bracket 180 and the dorsal mounting bracket 180, in turn, with respect to the body 150 as shown by the rotations $R_{LA}$, $R_{LB}$. The loosening of the hand adjustable knob 242 permits the rotation of both the mounting bracket 180 relative to the body 150 as shown by the rotation $R_{LB}$ and the armrest 184 relative to the mounting bracket 180 as shown by the rotation $R_{LA}$. The tightening of the hand adjustable knob 242 locks the rotational positions represented by the rotations $R_{LB}$, $R_{LA}$ in place. Similarly, the hand adjustable knob 244 is coupled to the dorsal mounting bracket 190 to permit control and positioning of the armrest member 194 with respect to the dorsal mounting bracket 190 and the dorsal mounting bracket, in turn, with respect to the body 150 as shown by the rotations $R_{RA}$, $R_{RB}$. The loosening of the hand adjustable knob 244 permits the rotation of both the mounting bracket 190 relative to the body 150 as shown by the rotation $R_{RB}$ and the armrest 194 relative to the mounting bracket 190 as shown by the rotation $R_{RA}$. The tightening of the hand adjustable knob 244 locks the rotational positions represented by the rotations $R_{RB}$, $R_{RA}$ in place. With the hand adjustable knobs 242, 244 loosened, the armrests 184, 194 may each be rotated and moved toward or away from each other by way of the rotations at the dorsal glides 186, 187, 196, 197. Once the position of the armrests 184, 194 is as desired, the hand adjustable knobs 242, 244 may be tightened to lock the desired positions of the armrests 184, 194.

The use of the surgical armrest 10 as part or component of a larger surgical system will now be discussed. With reference to FIG. 1 through FIG. 12, during some operational embodiments, the selectively moveable clamp 72 is attached to the vertical support arm 74, and both components are sterilized as a unit prior to surgery to be provided to the scrub technician by a circulating OR nurse, according to standard operating room protocol. When the surgeon wishes to attach the selectively moveable clamp 72 with the vertical support arm 74 to one of the arcuate rail members 90, 92, he or she first actuates the knob 126 from an engaged position to a released position. The surgeon then simply holds the cylindrical sheath 132 of the vertical support arm 74 with the selectively moveable clamp 72 attached, such that the selectively moveable clamp 72 hovers over the appropriate arcuate rail member 90, 92. It should be noted that the arcuate rail members 90, 92 would be approximately at knee level and are therefore not to be considered sterile. It should also be appreciated that an example of such movement of the selectively moveable clamp 72 is depicted in FIG. 1 through FIG. 5 wherein the selectively moveable clamp 72 is affixed to the arcuate rail member 90 in FIG. 1 and FIG. 3 through FIG. 5, while FIG. 2 includes the selectively moveable clamp 72 affixed to the arcuate rail member 92. As discussed herein, the selectively moveable clamp 72 may be moved between the arcuate rail member 90 and the arcuate rail member 92, as required, in those embodiments of the base station 70 having two arcuate rail members 90, 92. The circulating operating room nurse can assist the surgeon in this process by taking hold of the selectively moveable clamp 72 at the body 110, guiding the body 110 so that the arcuate rail member 90 or arcuate rail member 92 is accepted within. The surgeon then actuates the knob 126 from a release position to an engaged position, once the vertical support arm 74 has been moved to a desired location on the desired arcuate rail 90 or 92 for attaching and employing the armrest 10.

Moreover, with some practice, the surgeon will likely be able to connect the selectively moveable clamp 72 already attached to the vertical support arm 74 to the base station 70 without any external help. Accordingly, with the control knob 126 in the "loosened" release position, the surgeon can move the entire selectively moveable clamp 72 with the vertical support arm 74 onto one of the arcuate rails 90, 92 around the base station 70 attached to the operating room table 14 by moving the top of the vertical support arm 74. Standard operating room protocol considers surgical drapes to be sterile above a horizontal plane that approximates the bottom edge of the operating room tabletop 20, below which surgical sterility is assumed questionable. Scrubbed operating room personnel are taught that they are considered sterile down to their waist, but not below. Similarly, the base station assembly 12 should be considered sterile down to this same approximate level, and the surgical team must avoid contaminating themselves by touching the lower parts of the base station assembly 12. Indeed, the lower half of the vertical support arm 74 may have a different color or a distinctive brushed or ribbed finish as a reminder that this area is not considered sterile. This should not present any problem, however, since the operating room team should already know that one cannot lower his or her arms below the waist or touch an operating room gown below the individual's waist.

Figure 16:
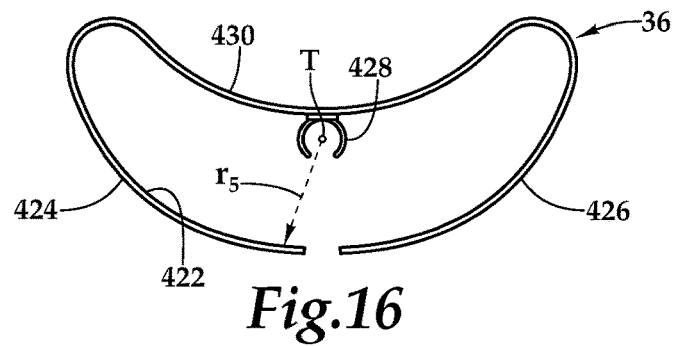
FIG. 16 is a top plan view of a drape holder, which in some embodiments, forms a portion of the base station, with an arcuate internal space in which the surgical drape falling from the patient's head is collected, thereby providing the surgeon a clear view of both arcuate rails for the docking of a selectively moveable clamp onto one or the other arcuate rail in order to support a surgical armrest according to the teachings presented herein.

It is suggested that the bottoms of the drapes that fall naturally from the draping of the patient's head be gathered with sterile gloves by a circulating operating room person and tucked inside the circular space defined by the arcuate rail member 90 of the base station 12. In this way, both arcuate rail members 90, 92 can be seen by the surgeon, and the selectively moveable clamps 72 and their respective vertical support arms 74 can be attached and moved about their respective arcuate rail members as the surgeon so desires from the start of surgery and throughout the operative procedure. If the surgeon requires the height of the operating room table 14 to be unusually high, the tails of the surgical drapes may end above the height of the arcuate rail member 90, which would normally hold the drapes out of the way, as discussed previously. With reference to FIG. 16 and FIG. 17, in a further alternative, the drape holder 36 clamps onto the vertical support 58 above the arcuate rail 90. With the drape holder 36 already in place and after the patient has been prepped and draped, the OR circulating nurse, wearing sterile gloves, can collect the hanging ends of the surgical drape from the patient's head and introduce them into the arcuate space defined by the drape holder 36, thereby moving the drapes away from the inner surface of the arcuate rail 90. This process may improve the surgeon's vision of the arcuate rail 90 and simplify the process of placing the selectively moveable clamp 72 onto the arcuate rail 90. Without using the drape holder 36, the drapes hanging from the head, now wet from surgical irrigation and blood, may fold over, adhere to, or obscure some areas of the arcuate rail 90. At worse, this may obscure the surgeon's placement of the selectively moveable clamp 72 on the arcuate rail 90. At best, this situation may require the circulating OR staff to try to reposition wet and bloody drapes for the surgeon to see adequately the arcuate rail 90. Accordingly, utilizing the arcuate rail 90 to control the drapes so as not to interfere with the process of docking the selectively moveable clamps 72 may prove to be more difficult or inadequate.

Once the surgeon has attached the selectively moveable clamp 72 to the base station 70, the surgeon can make positioning adjustments of the surgical armrest 10 then or at any subsequent time during surgery without external help. This feature provides remarkable adjustability of surgical accessories such as brain retractors and the surgical armrest—all controlled by the surgeon without requiring assistance from the circulating operating room nursing staff. Simply loosening the control knob 126 on the vertical support arm 74 allows the surgeon to move an accessory such as the surgical armrest 10 around a circular orbit of the center axis of the arcuate rails 90, 92 of the base station 70, if required during surgery, and this procedure can be quickly and easily repeated whenever necessary. Moreover, the surgeon can rotate the elongated member 116 on itself where it connects to the dorsal aspect of the selectively moveable clamp 72. Because of the curve S configuration of the elongated member 116, such rotation would bring an accessory—the surgical armrest 10, for example—closer or farther away from the operative site, and it may be necessary to adjust the radial position of the selectively moveable clamp 72 on the base station 70 as part of this maneuver. Furthermore, if desired by the surgeon, the elongated member 116 can be tilted slightly as it is pivoted on its attachment for more subtle adjustment which can be maintained by tightening the control knob 126 to lock the elongated member 116 and the selectively moveable clamp 72 in position.

As alluded, at the end 118 of the elongated member 116, the height of the vertical support arm 74 can be extended and then locked in place with the control knob 128. Indeed, the length of the vertical support arm 74 may be manufactured at whatever length is comfortable for the users, and different sized embodiments can be kept sterile to address surgeon preference. For instance, perhaps a visiting surgeon is requested to help the surgical team on a complex operation, and on his arrival in the OR, this very tall surgeon requests that the height of surgical armrest 10 be adjusted beyond the limit of the vertical support arm 74 presently in use. The circulating OR nurse opens the wrapping of a previously sterilized support arm 74 of correct length, which is already connected to a selectively moveable clamp 72, and the scrub technician hands the device to the guest surgeon, who is scrubbed, gowned, and gloved. Holding the device by its cylindrical sheath 132, the guest surgeon turns to the OR table and positions the selectively moveable clamp 72 to hover exactly over the arcuate rail 90. He then carefully lowers the device to dock the selectively moveable clamp 72 with the desired long support arm 74 onto the arcuate rail 90. The surgeon can then push the device along the arcuate rail 90 into the needed radial position, but he then realizes positioning would be optimized if he tilted the support arm 74 a few degrees, which he does. He then tightens the control knob 126, which locks in place the selectively moveable clamp 72 and the long support arm 74 to the arcuate rail 90 with just the right tilt. All of these adjustments were first actuated and then locked into place with control knob 126, surely taking less than 5 minutes. A sterile surgical armrest 10 is transferred onto the long support arm 74, and surgery can continue.

Once the length of the vertical support arm 74 is set, at any time during surgery, the dorsal-to-ventral tilt D-V of the surgical armrest 10 may be adjusted with the control knob 240; angle of rotation, with the control knob 248; axial position of the surgical armrest 10 on the arcuate rail 90, 92, with the control knob 126; up to 360° rotation of the vertical support arm 74 as well as fine tuning of tilt of the vertical support arm 74 at the bottom end 120 of the elongated member 116 to approximately 7° in any direction above the plane of the upper end 132 of the selectively moveable clamp 72, also with the control knob 126; and almost unrestricted lateral tilt of the surgical armrest so that one hand and forearm can be higher than the other, with the control knob 246. It is estimated that each of these positional adjustments can be accomplished in just a few seconds.

Accordingly, positional adjustment of the surgical armrest 10 is set with the hand adjustable knobs 240, 246, 248, 128, 126. The configuration of the surgical armrest 10 and, in particular, the armrest members 184, 194 are then set with the hand adjustable knobs 242, 244. Importantly, the surgical armrest 10 may be adjusted to accommodate physical characteristics of the surgeon, such as height, weight, and body habitus, that impact the ergonomics of arm, forearm, and wrist placement. The surgical armrest 10 may also be adjusted to accommodate characteristics of the operating environment. By way of example, the hand adjustable knob 240 permits nod and in/out adjustments to the surgical armrest 10. The hand adjustable knobs 242, 244 loosen and lock the armrests 184, 194 to provide the desired rotation and movement toward and away from each other. The hand adjustable knob 246 provides for side-to-side tilt and the hand adjustable knob 248 provides for rotation of the surgical armrest 10 around the axis of vertical support arm 74. Each of the hand adjustable knobs 240, 242, 244, 246, 248 may be adjusted and re-adjusted as needed during a surgical procedure to ensure surgeon comfort. For example, to accomplish a somewhat awkward maneuver, the surgeon may wish to adjust the surgical armrest 10 so that one of the surgeon's hands is slightly higher than the other.

Moreover, various selectively moveable clamps 72 with vertical support arms 74 can be added to or removed from the base station 70 as needed without having to struggle with wet, bloody drapes. As discussed previously, by having gathered the surgical drapes together within the arcuate rail member 90 or alternatively, if the operating room table 14 is set to an unusually high position, the drapes can be gathered within a plastic drape holder device, both arcuate rail members 90, 92 are always easy for the surgeon to visualize in order to add or remove a selectively moveable clamp 72 with its attached vertical support arm 74 without assistance. The orbits of both arcuate rail members 90, 92 of the base station 70 remain freely accessible not only initially at the start of the operation, but also throughout the surgical procedure. After draping, the surgeon can determine how many selectively moveable clamps 72 and vertical support arms 74 are estimated to be needed for the procedure. These various vertical support arms 74 can be positioned where the surgeon thinks they will be required, or they can be clustered at either or both ends of the base station 70 to be moved into place later as needed. Alternatively, selectively moveable clamps 72 with vertical support arms 74 can be added or removed as necessary at any time during the surgery. It should be appreciated that the selectively moveable clamp 72 traffic may require forethought and planning. Having two arcuate rail members greatly facilitates this process.

Figure 13:
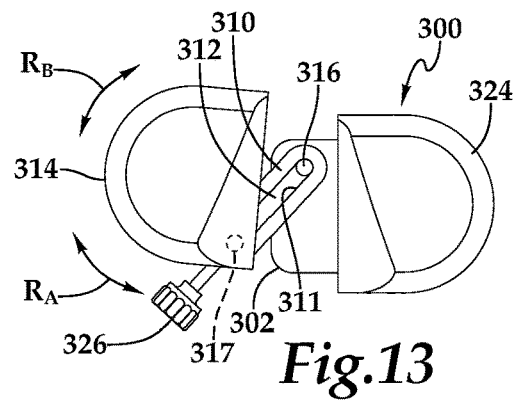
FIG. 13 is a dorsal plan view of another embodiment of a surgical armrest according to the teachings presented herein.

Referring now to FIG. 13, another embodiment of a surgical armrest 300 is depicted. The surgical armrest 300 includes a body 302, having a dorsal mounting bracket 310 having an elongated aperture 312, which may be a linear slot or an arcuate slot, for example, that is secured to the dorsal surface of the body 302. An armrest member 314 is secured to the dorsal mounting bracket 310 at the elongated aperture 312 by dorsal glides 316, 317. The armrest member 314 is configured to support a body part, such as an elbow, forearm, wrist, or combinations thereof. The elongated aperture 312 defines a range of rotation $R_B$ at the dorsal glide 316 and a range of rotation $R_A$ at the dorsal glide 317. Both ranges of rotation are substantially parallel to the body 302. The rotations $R_B$, $R_A$ may be activated by loosening a hand adjustable knob 326 which is coupled to the dorsal mounting bracket 310. Tightening of the hand adjustable knob 326 locks the positioning of the rotations $R_B$, $R_A$.

An armrest member 324 is statically secured to the dorsal surface of the body 302. In the static configuration, a dorsal mounting bracket may be secured to the dorsal surface of the body 302. The mounting bracket may have an aperture such that the armrest member 324 is statically secured to the dorsal mounting bracket at the aperture by a dorsal glide. The armrest member 324 is configured to support a body part, such as an elbow, forearm, wrist, or combination thereof. It should be appreciated that either one or both of the armrest members may be static and secured in place to the body 302.

Figure 14:
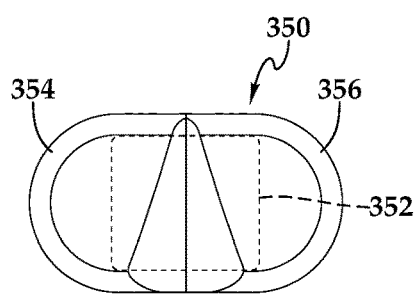
FIG. 14 is a dorsal plan view of a still further embodiment of a surgical armrest according to the teachings presented herein.

Referring now to FIG. 14, another embodiment of a surgical armrest 350 is depicted. The surgical armrest 350 includes a body 352 having armrest members 354, 356 secured thereto. The armrest member 354 is statically positioned and configured to support a body part, such as an elbow, forearm, wrist, or combinations thereof. Likewise, the armrest members 356 is statically positioned and secured to support a body part, such as an elbow, forearm, wrist, or combinations thereof. It should be appreciated that either one or both of the armrest members may be static and secured in place to the body. It should also be appreciated that either one or both of the armrest members may be dynamic.

Figure 15:
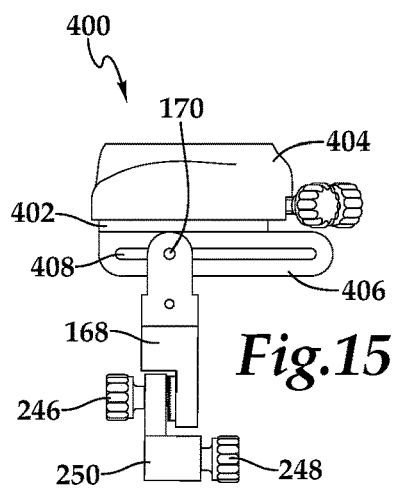
FIG. 15 is a lateral elevation view of an alternative embodiment of a surgical armrest according to the teachings presented herein.

Referring now to FIG. 15, in another embodiment, a surgical armrest 400 includes a body 402 having a pair of armrests 404 attached thereto. A ventral mounting bracket 406 extends from the body 402. An elongated slot 408 is provided in the ventral mounting bracket. As previously discussed, when operating on tiny babies such as small infants, term infants, or premature infants, the surgeon may require additional radial adjustment capability to position the surgical armrest 400 close enough to the surgical site so that the surgeon can operate with standard microsurgical instrumentation while resting his forearms and/or wrists on the surgical armrest 400. Therefore, in another embodiment that allows for this positioning adjustment in the caudal direction, the elongated slot 408 is extended cranially. It should be appreciated that the surgeon may prefer to use the surgical armrest 400 with the extended slot 408 on all patients.

Referring now to FIG. 16, as may be appreciated, during a surgical operation utilizing the surgical armrest 10, the bottoms of surgical drape that fall naturally from the draping of the head of the patient may be gathered and tucked inside the drape holder 36 having an arcuate space 422 defined by rostral retaining members 424, 426, and caudal retaining member 430. The drape holder 36 is adjustably secured to the vertical support member 58 by a support member 428. In one embodiment, a radius $r_1$, which is proximate to a center T, of the drape holder 36 is less than the radius of the rail member 90 and the radius of the rail member 92. This permits the surgical drape to be gathered and groomed so as not to interfere with the surgical procedure or use of the base station assembly 12.

Figure 2:
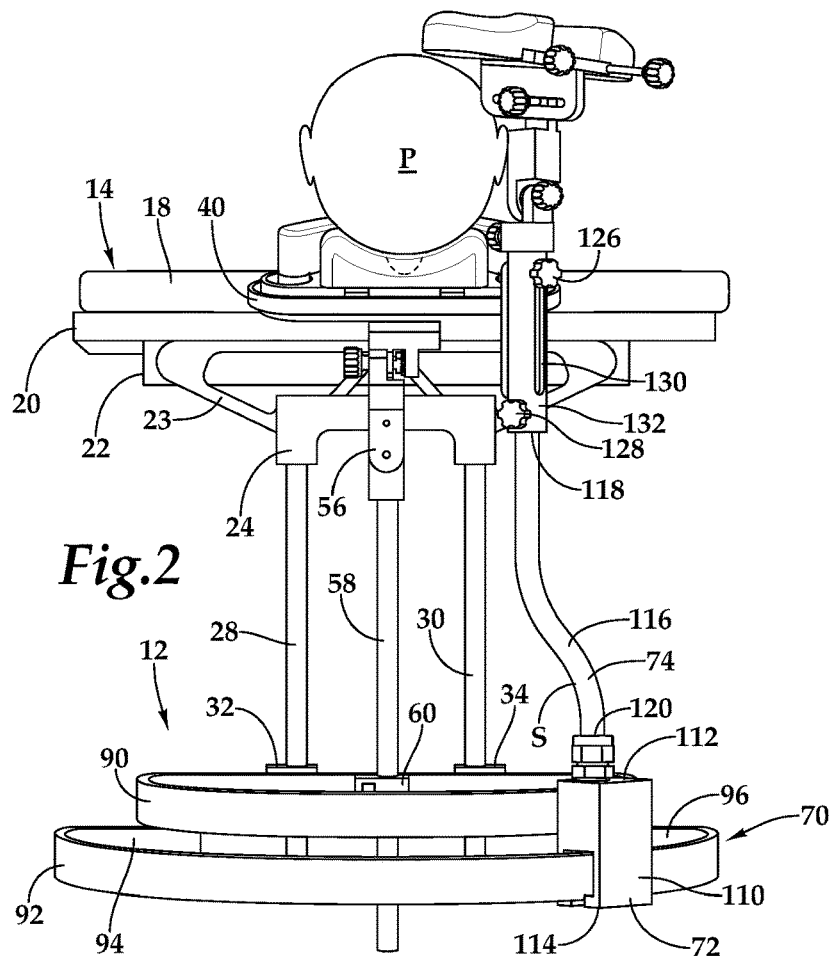
FIG. 2 is a cephalic elevation view of one embodiment of the cranial end of the operating room table with the surgical head holder and the base station assembly to facilitate the use of a surgical armrest, during the surgical procedure, with some components removed, to provide a better view of the surgical armrest for purposes of explanation.
Figure 3:
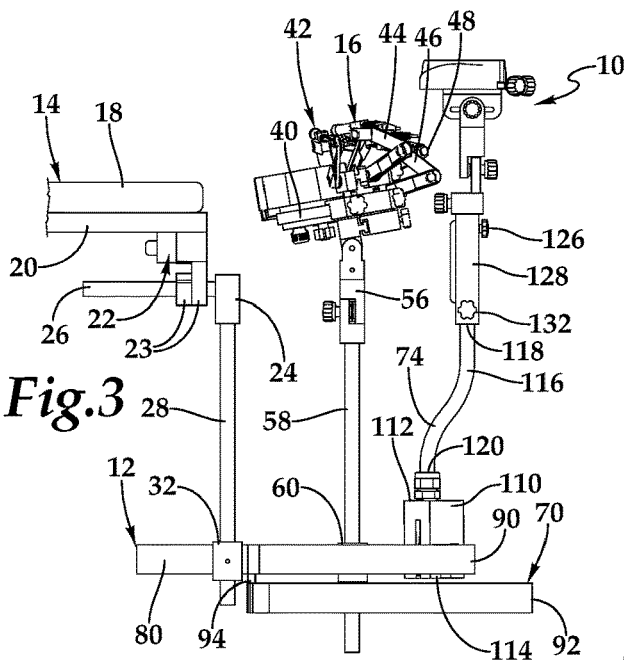
FIG. 3 is a lateral elevation view of the operating room table with the surgical head holder, the base station assembly, and the surgical armrest depicted in FIG. 1, without the patient.
Figure 5:
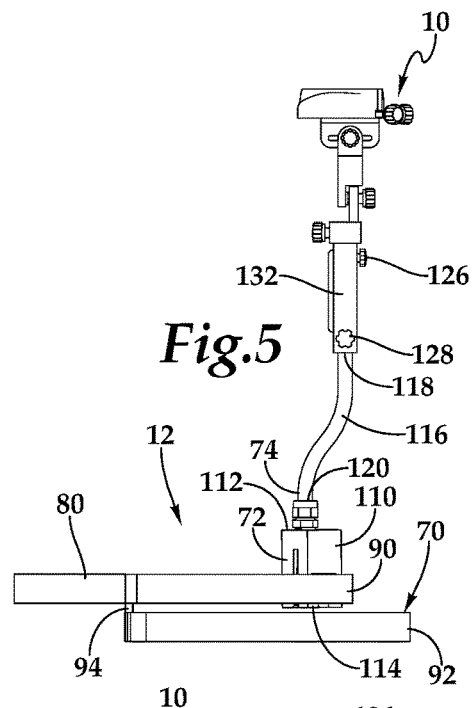
FIG. 5 is a lateral elevation view of the base station assembly and the surgical armrest depicted in FIG. 1.
Figure 4:
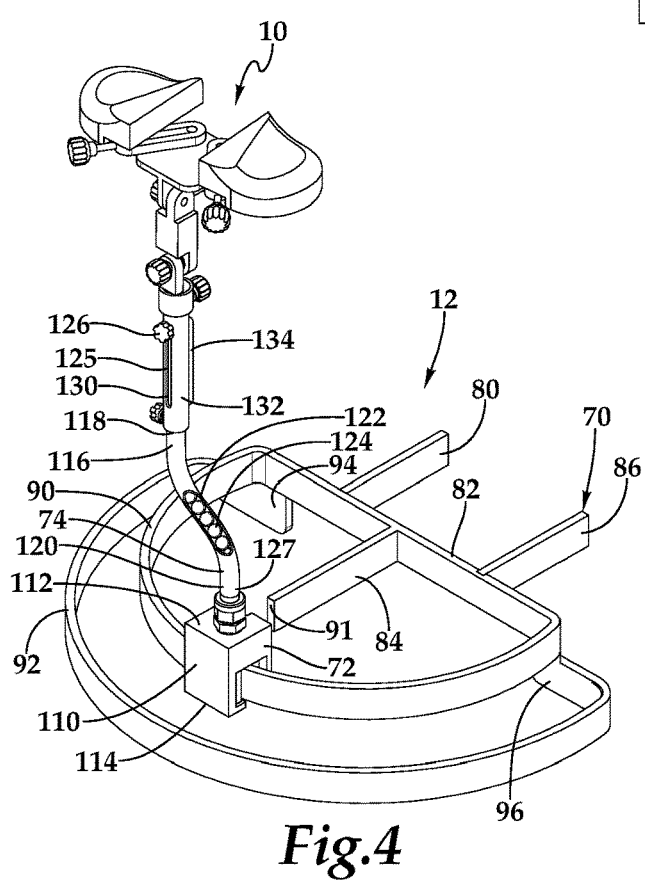
FIG. 4 is a dorsal cephalic perspective view of the base station assembly and the surgical armrest depicted in FIG. 1.
Figure 6:
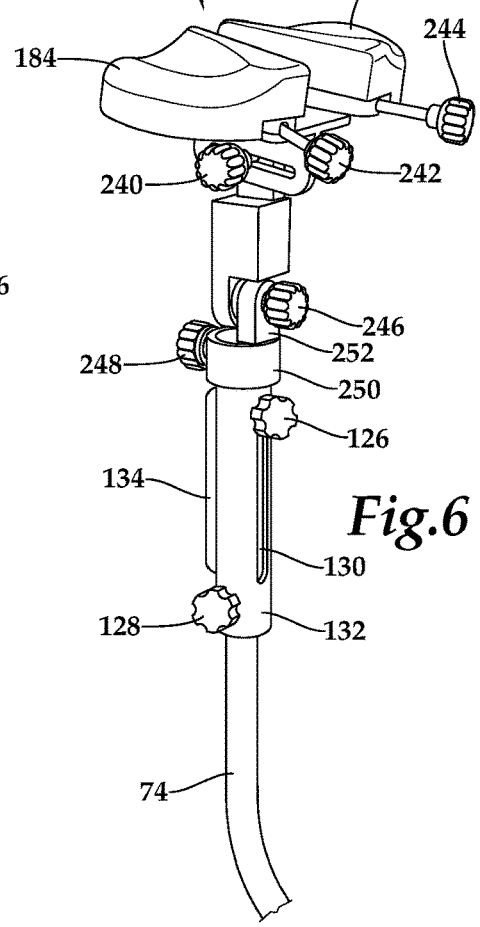
FIG. 6 is a dorsal cephalic perspective view of the surgical armrest depicted in FIG. 1 extending from the base station assembly (not fully shown in FIG. 6)

With reference to FIG. 2, FIG. 3, and FIG. 17, in some embodiments, a center point base station configuration 500 for the base station 70 may be employed for patients ranging from children to adults, where the cross bar 24 is positioned rostral to the horizontal support member 22 of the OR table 12 and the "W" table brace 23, best seen in FIG. 2. Such a design provides a maximal arcuate excursion of, by way of example, 286° of mobility for the selectively moveable clamp 72 on the upper arcuate rail 502 and, by way of example, a 274° excursion on the lower arcuate rail 504, as summarized in FIG. 17, with the mobility illustrated by arrows 510, 512. As shown, the selectively moveable clamp 72 is appropriately positionable and repositionable about the patient P resting on gel pads 514 of the headrest 40. Pins and other components have been omitted for clarity.

The order of execution or performance of the methods and process flows illustrated and described herein is not essential, unless otherwise specified. That is, elements of the methods and process flows may be performed in any order, unless otherwise specified, and that the methods may include more or less elements than those disclosed herein. For example, it is contemplated that executing or performing a particular element before, contemporaneously with, or after another element are all possible sequences of execution.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. A surgical armrest comprising:
   a body having a dorsal surface, a ventral surface, a first lateral end, a second lateral end, a caudal end, and a cephalic end, the body having a horizontal axis therethrough, the body having a vertical axis therethrough, the horizontal axis being perpendicular to the vertical axis, the body having a medial line between the first lateral end and the second lateral end;
   a ventral mounting bracket being secured to the ventral surface of the body, the ventral mounting bracket including an elongated slot defining a range of caudal-to-cephalic sliding motion of the body with respect to a support member which is secured thereto, the elongated slot defining a range of dorsal-to-ventral tilt of the body with respect to the support member, the elongated slot being perpendicular to the horizontal axis;
   a first dorsal mounting bracket being secured to the dorsal surface of the body, the first dorsal mounting bracket having a first elongated aperture with first and second dorsal glides therein with a first linking lock bar therebetween;
   a first armrest member being secured to the first dorsal mounting bracket at the first elongated aperture by the first dorsal glide, the first armrest member having a first range of rotation with respect to the first dorsal mounting bracket, the first dorsal mounting bracket having a second range of rotation with respect to the body;
   a second dorsal mounting bracket being secured to the dorsal surface of the body, the second dorsal mounting bracket having a second elongated aperture with third and fourth dorsal glides therein with a second linking lock bar therebetween;

a second armrest member being secured to the second dorsal mounting bracket at the second elongated aperture by the third dorsal glide, the second armrest member having a third range of rotation with respect to the second dorsal mounting bracket, the second dorsal mounting bracket having a fourth range of rotation with respect to the body;

the first armrest member having a first elevated portion and a first concave portion; and the second armrest member having a second elevated portion and a second concave portion.

2. The surgical armrest as recited in claim 1, wherein the first armrest member is configured to support a body part selected from the group consisting of elbows, forearms, wrists, and combinations thereof.

3. The surgical armrest as recited in claim 1, wherein the second armrest member is configured to support a body part selected from the group consisting of elbows, forearms, wrists, and combinations thereof.

4. The surgical armrest as recited in claim 1, wherein the first dorsal mounting bracket is secured to the dorsal surface of the body proximate the caudal end between the medial line and the first lateral end.

5. The surgical armrest as recited in claim 1, wherein the second dorsal mounting bracket is secured to the dorsal surface of the body proximate the caudal end between the medial line and the second lateral end.

6. The surgical armrest as recited in claim 1, wherein the first armrest member and the second armrest member further comprise a closed position wherein the first elevated portion and the second elevated portion are adjacent.

7. The surgical armrest as recited in claim 1, wherein the first elevated portion and the second elevated portion have complimentary forms.

8. The surgical armrest as recited in claim 1, further comprising a hand adjustable knob coupled to the ventral glide, the hand adjustable knob controlling a position of the body with respect to the support member.

9. The surgical armrest as recited in claim 1, further comprising a hand adjustable knob coupled to the first dorsal mounting bracket, the hand adjustable knob permitting control of the first range of motion and the second range of motion.

10. The surgical armrest as recited in claim 1, further comprising a hand adjustable knob coupled to the second dorsal mounting bracket, the hand adjustable knob permitting control of the third range of motion and the fourth range of motion.

11. The surgical armrest as recited in claim 1, wherein the elongated slot further comprises a shape selected from the group of linear slots and arcuate slots.

12. The surgical armrest as recited in claim 1, wherein the first elongated aperture further comprises a shape selected from the group of linear slots and arcuate slots.

13. The surgical armrest as recited in claim 1, wherein the second elongated aperture further comprises a shape selected from the group of linear slots and arcuate slots.

14. A surgical armrest comprising:
a body having a dorsal surface, a ventral surface, a first lateral end, a second lateral end, a caudal end, and a cephalic end;
a ventral mounting bracket being secured to the ventral surface of the body, the ventral mounting bracket providing a range of caudal-to-cephalic sliding motion of the body with respect to a support member which is secured thereto, the ventral mounting bracket providing a range of dorsal-to-ventral tilt of the body with respect to the support member;
a first dorsal mounting bracket being secured to the dorsal surface of the body, the first dorsal mounting bracket having a first range of rotation with respect to the body;
a first armrest member being secured to the first dorsal mounting bracket, the first armrest member having a second range of rotation with respect to the first dorsal mounting bracket;
a second dorsal mounting bracket being secured to the dorsal surface of the body, the second dorsal mounting bracket having a third range of rotation with respect to the body; and
a second armrest member being secured to the second dorsal mounting bracket, the second armrest member having a fourth range of rotation with respect to the second dorsal mounting bracket.

15. The surgical armrest as recited in claim 14, wherein the first armrest member is configured to support a body part selected from the group consisting of elbows, forearms, wrists, and combinations thereof.

16. The surgical armrest as recited in claim 14, wherein the second armrest member is configured to support a body part selected from the group consisting of elbows, forearms, wrists, and combinations thereof.

17. A surgical armrest comprising:
a body having a dorsal surface, a ventral surface, a first lateral end, a second lateral end, a caudal end, and a cephalic end, the body having a horizontal axis therethrough, the body having a vertical axis therethrough, the horizontal axis being perpendicular to the vertical axis, the body having a medial line between the first lateral end and the second lateral end;
a first dorsal mounting bracket being secured to the dorsal surface of the body, the first dorsal mounting bracket having a first range of rotation with respect to the body;
a first armrest member being secured to the first dorsal mounting bracket, the first armrest member having a second range of rotation with respect to the first dorsal mounting bracket; and
a second dorsal mounting bracket being secured to the dorsal surface of the body, the second dorsal mounting bracket statically securing a second armrest thereto.

18. The surgical armrest as recited in claim 17, wherein the first armrest member is configured to support a body part selected from the group consisting of elbows, forearms, wrists, and combinations thereof.

19. The surgical armrest as recited in claim 17, wherein the second armrest member is configured to support a body part selected from the group consisting of elbows, forearms, wrists, and combinations thereof.

20. A surgical armrest comprising:
a body having a dorsal surface, a ventral surface, a first lateral end, a second lateral end, a caudal end, and a cephalic end, the body having a horizontal axis therethrough, the body having a vertical axis therethrough, the horizontal axis being perpendicular to the vertical axis, the body having a medial line between the first lateral end and the second lateral end;
a first armrest member being secured to the dorsal surface;
a second armrest member being secured to the dorsal surface;
the first armrest member having a first elevated portion and a first concave portion; and the second armrest member having a second elevated portion and a second concave portion.

* * * * *